United States Patent
Beppu et al.

(10) Patent No.: US 11,207,258 B2
(45) Date of Patent: Dec. 28, 2021

(54) CAPSULE CONTAINING FUNCTIONAL SUBSTANCE AND METHOD FOR MANUFACTURING SAID CAPSULE

(71) Applicant: SUNTORY HOLDINGS LIMITED, Osaka (JP)

(72) Inventors: Yoshinori Beppu, Kyoto (JP); Yoshihide Matsuo, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 145 days.

(21) Appl. No.: 16/072,330

(22) PCT Filed: Jan. 25, 2017

(86) PCT No.: PCT/JP2017/002464
§ 371 (c)(1),
(2) Date: Jul. 24, 2018

(87) PCT Pub. No.: WO2017/131003
PCT Pub. Date: Aug. 3, 2017

(65) Prior Publication Data
US 2019/0029940 A1 Jan. 31, 2019

(30) Foreign Application Priority Data
Jan. 25, 2016 (JP) .............................. JP2016-011485

(51) Int. Cl.
| | | |
|---|---|---|
| *A61K 8/65* | (2006.01) | |
| *A61Q 19/00* | (2006.01) | |
| *C08J 3/24* | (2006.01) | |
| *A23L 5/00* | (2016.01) | |
| *A61K 8/41* | (2006.01) | |
| *C08J 3/12* | (2006.01) | |
| *B01J 13/14* | (2006.01) | |
| *A23P 10/00* | (2016.01) | |
| *A23L 29/281* | (2016.01) | |
| *A61K 8/11* | (2006.01) | |
| *A61K 8/73* | (2006.01) | |
| *B01J 13/20* | (2006.01) | |
| *A61K 9/48* | (2006.01) | |

(52) U.S. Cl.
CPC ............... *A61K 8/65* (2013.01); *A23L 5/00* (2016.08); *A23L 29/284* (2016.08); *A23P 10/00* (2016.08); *A61K 8/11* (2013.01); *A61K 8/41* (2013.01); *A61K 8/73* (2013.01); *A61Q 19/00* (2013.01); *B01J 13/14* (2013.01); *B01J 13/20* (2013.01); *C08J 3/12* (2013.01); *C08J 3/24* (2013.01); *A23V 2002/00* (2013.01); *A61K 9/4866* (2013.01); *C08J 2389/06* (2013.01)

(58) Field of Classification Search
CPC . A61K 8/65; A61K 8/11; A23L 29/284; C08J 3/24; B01J 13/14
See application file for complete search history.

(56) References Cited

U.S. PATENT DOCUMENTS

| | | | |
|---|---|---|---|
| 6,203,804 B1 * | 3/2001 | Murakado | A61K 8/73 424/401 |
| 6,831,058 B1 | 12/2004 | Ikada et al. | |
| 2008/0003292 A1 | 1/2008 | Ahlers et al. | |
| 2010/0087626 A1 | 4/2010 | Ooya et al. | |
| 2014/0179803 A1 | 6/2014 | Van Den Broek et al. | |
| 2014/0316013 A1 | 10/2014 | Sugawara et al. | |
| 2016/0121025 A1 | 5/2016 | Yamashita et al. | |

FOREIGN PATENT DOCUMENTS

| | | | | |
|---|---|---|---|---|
| CN | 101020061 A | * | 8/2007 | |
| CN | 102470106 A | | 5/2012 | |
| CN | 103951832 A | * | 7/2014 | |
| CN | 104109252 A | | 10/2014 | |
| CN | 103933012 B | * | 11/2015 | |
| CN | 105247041 A | | 1/2016 | |
| GB | 2224258 A | * | 5/1990 | ........... A61K 9/1658 |
| JP | H02-167222 A | | 6/1990 | |
| JP | 2007-144282 A | | 6/2007 | |
| JP | 2007-226059 A | | 9/2007 | |
| JP | 2008-510688 A | | 4/2008 | |
| JP | 2014-527028 A | | 10/2014 | |
| WO | WO-94/27630 A1 | | 12/1994 | |
| WO | WO-2008/072379 A1 | | 6/2008 | |
| WO | WO-2010/133609 A2 | | 11/2010 | |

OTHER PUBLICATIONS

Adhirajan, N. et al. "Gelatin microspheres cross-linked with EDC as a drug delivery system for doxycyline: Development and characterization" Journal of Microencapsulation, Nov. 2007; 24(7): 659-671 (Year: 2007).*
Shimadzu (https://www.shimadzu.com/an/industry/foodbeverages/n9j25k00000dqazu.htm), pp. 1-3, accessed Jun. 3, 2020 (Year: 2020).*
Chang, J-Y. et al. "In Vivo Evaluation of a Biodegradable EDC/NHS-Cross-Linked Gelatin Peripheral Nerve Guide Conduit Material" Macromol. Biosci. 2007, 7, 500-507 (Year: 2007).*
Shuai et al. CN 103951832A; machine translation, pp. 1-6 (Year: 2014).*
Gelatin Handbook (https://pdfs.semanticscholar.org/d55b/cf1e26fb6f1caeb88b1ac95d1bda78c79db4.pdf) Jan. 2012, pp. 1-25 (Year: 2012).*

(Continued)

*Primary Examiner* — Andrew S Rosenthal
(74) *Attorney, Agent, or Firm* — Faegre Drinker Biddle & Reath LLP

(57) ABSTRACT

It is an object of the present invention to provide a capsule comprising a functional substance and having good shape stability and a good feeling of use. A method for producing a capsule, comprising steps of mixing gelatin and a functional substance; adding a carbodiimide crosslinking agent to crosslink the gelatin with the carbodiimide crosslinking agent; solidifying the crosslinked gelatin; and grinding the solidified gelatin.

8 Claims, 1 Drawing Sheet

(56) References Cited

OTHER PUBLICATIONS

FoodComEx (https://foodcomex.org/compounds/FDB002613), pp. 1-6, accessed Oct. 23, 2020 (Year: 2020).*
He, J. et al. "Anthocyanins: Natural Colorants with Health-Promoting Properties" Annu. Rev. Food Sci. Technol. 2010. 1:163-87 (Year: 2010).*
Machine translation of CN103933012B, pp. 1-8, accessed Oct. 23, 2020 (Year: 2020).*
Harikumar, K.B. et al. "Sesamin Manifests Chemopreventive Effects through the Suppression of NF-κB-Regulated Cell Survival, Proliferation, Invasion, and Angiogenic Gene Products" Mol Cancer Res; 8(5) May 2010 (Year: 2010).*
Berger, S. et al. "Microgel-Based Stimuli-Responsive Capsules" Adv. Funct. Mater. 2009, 19, 554-559 (Year: 2009).*
Machine translation of CN101020061A, pp. 1-10, accessed Oct. 23, 2020 (Year: 2020).*
N. Adhirajan et al., "Gelatin microspheres cross-linked with EDC as a drug delivery system for doxycyline: Development and characterization," Journal of Microencapsulation, Nov. 2007, pp. 659-671, vol. 24, No. 7.
International Search Report dated Apr. 11, 2017 for PCT/JP2017/002464.

* cited by examiner

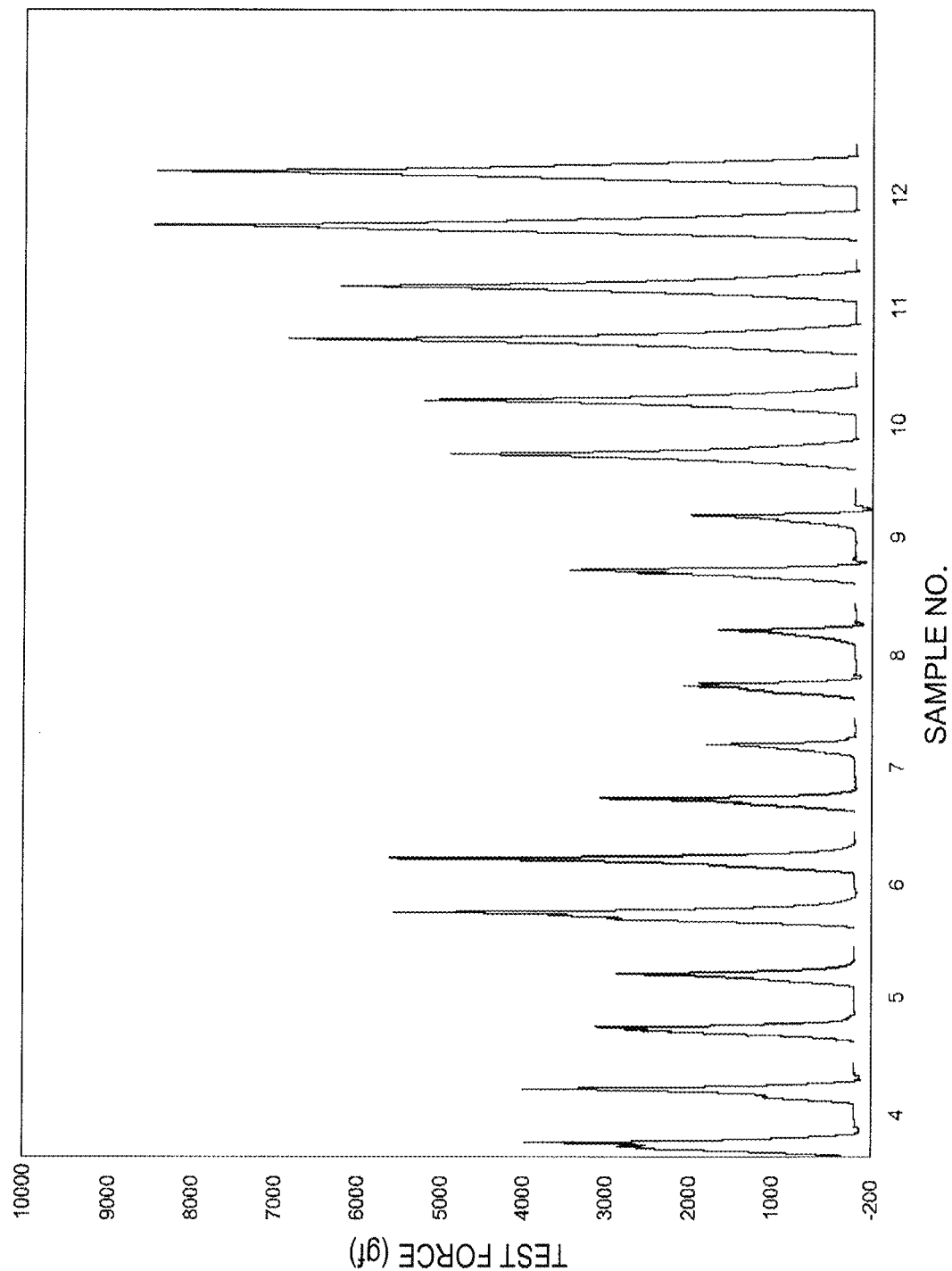

CAPSULE CONTAINING FUNCTIONAL SUBSTANCE AND METHOD FOR MANUFACTURING SAID CAPSULE

CROSS REFERENCES TO RELATED APPLICATIONS

This application is the National Stage of International Application No. PCT/JP2017/002464 filed Jan. 25, 2017, and claims benefit of Japanese Application No. 2016-011485 filed on Jan. 25, 2016.

TECHNICAL FIELD

The present invention relates to a capsule comprising a functional substance, and a method for producing the same. More particularly, the present invention relates to a crosslinked gelatin capsule comprising a functional substance, and a method for producing the same.

BACKGROUND ART

So far, various functional substances have been discovered from natural materials or artificially synthesized, and utilized in various fields of foods and drinks, cosmetics, drugs, and the like. But, many functional substances have properties such as being unstable to acids, alkalis, heat, oxygen, or the like or being not good in solubility or dispersibility in solvents. Therefore, the use of functional substances may be limited. As means for addressing this problem, techniques regarding shell type capsules in which a functional substance is wrapped in a capsule for stabilization, and the capsule is broken when needed, to release the contents are known, and techniques regarding crosslinked capsules in which the wall substance of a capsule is crosslinked with a crosslinking agent are reported. For example, a method of crosslinking a biopolymer with a crosslinking agent such as transglutaminase to obtain a capsule having high strength is known (Patent Literature 1).

CITATION LIST

Patent Literature

PTL 1: WO2008/072379

SUMMARY OF INVENTION

Technical Problem

However, in some capsules having high strength, functional substances may not suitably be released during use. When a capsule having high strength is applied to the skin or the like, it does not fit comfortably on skin; or it causes roughness feeling on skin. Thus, there is room for improvement in the feeling of use of such a capsule. When a capsule having high strength is applied to a food or a drink, there is room for improvement in the rough mouthfeel during eating, the release of the functional substance, and the like. It is an object of the present invention to provide a capsule having a good feeling of use that can be easily broken in use while having strength sufficient to maintain its shape even if the capsule is stored for a long period.

Solution to Problem

In order to solve the above problems, the present inventors have studied diligently, and as a result found that by crosslinking gelatin that is a wall agent of a capsule with a carbodiimide crosslinking agent, the shape of the capsule is stabilized. The present inventors have also found that the capsule can be easily collapsed during use and has a good feeling of use. The present invention has been completed based on the matters.

Specifically, the present invention provides, but is not limited to, the following.

(1) A method for producing a capsule, comprising steps of:
mixing gelatin and a functional substance;
adding a carbodiimide crosslinking agent to crosslink the gelatin with the carbodiimide crosslinking agent;
solidifying the crosslinked gelatin; and
grinding the solidified gelatin.

(2) The production method according to (1), wherein the gelatin is crosslinked in a solution comprising the carbodiimide crosslinking agent at a concentration of 5 mM to 200 mM.

(3) The production method according to (1) or (2), wherein the gelatin and the carbodiimide crosslinking agent are reacted at a concentration ratio of 1:0.06 to 1:0.2.

(4) The production method according to any of (1) to (3), wherein the carbodiimide crosslinking agent is selected from the group consisting of 1-ethyl-3-(3-dimethylaminopropyl)carbodiimide, 1-cyclohexyl-3-(2-morpholinyl-4-ethyl)carbodiimide, dicyclohexylcarbodiimide, diisopropylcarbodiimide, and salts thereof.

(5) The production method according to any of (1) to (4), wherein the gelatin has a jelly strength of 100 g or more.

(6) A capsule comprising a functional substance, and gelatin crosslinked with a carbodiimide crosslinking agent.

(7) The capsule according to (6), wherein the gelatin has a jelly strength of 100 g or more.

(8) The capsule according to (6) or (7), wherein the gelatin is acid-treated gelatin.

Advantageous Effects of Invention

A capsule obtained by crosslinking gelatin with a carbodiimide crosslinking agent is easily collapsed and suitably releases the included functional substance during use while being stable for a long period, and also has a good feeling of use. The capsule can be used for external preparations for skin such as cosmetics and quasi-drugs, and foods and drinks.

BRIEF DESCRIPTION OF DRAWING

FIG. 1 shows the texture of capsules.

DESCRIPTION OF EMBODIMENTS

<Capsule>

A capsule as referred to herein comprises a capsule comprising gelatin and a carbodiimide crosslinking agent, and a functional substance included in the capsule. Although not bound by theory, by including the functional substance in the capsule, contact between the functional substance and a substance or an environment that hinders the activity and stability of the functional substance can be avoided, and/or the solubility or dispersibility of the functional substance in a solvent can be improved.

Functional Substance

The "functional substance" in the present invention should be a substance that can be included in the capsule of the present invention, and can be appropriately selected according to the purpose of use. One that provides some benefit such as the maintenance of activity and stability or the improvement of dispersibility or solubility by being included in the capsule is preferably selected as the functional substance. The functional substance can be selected based on the water solubility of a substance, and preferably a substance having low water solubility is selected. Here, the substance having low water solubility refers to a substance poorly soluble in water (the amount of a solvent necessary to dissolve 1 g of a solute is 100 mL or more and less than 1000 mL (Nihon Yakkyokuho Kaisetsusho (Manual of the Japanese Pharmacopoeia)), a substance extremely poorly soluble in water (the amount of a solvent necessary to dissolve 1 g of a solute is 1000 mL or more and less than 10000 mL (Nihon Yakkyokuho Kaisetsusho (Manual of the Japanese Pharmacopoeia)), or a substance hardly soluble in water (the amount of a solvent necessary to dissolve 1 g of a solute is 10000 mL or more (Nihon Yakkyokuho Kaisetsusho (Manual of the Japanese Pharmacopoeia)). The water solubility of the substance that can be selected as the functional substance should be, for example, 10 g/L or less, 5 g/L or less, 2 g/L or less, 1.5 g/L or less, or 1.0 g/L or less. It is not necessary to set the lower limit of the water solubility, but if illustrated, it may be 0.0001 g/L or more, 0.001 g/L or more, or 0.005 g/L or more. The functional substance can also be selected based on the octanol/water distribution coefficient (Log Pow) of a substance. For example, a substance having an octanol/water distribution coefficient of 1.0 or more, 1.2 or more, or 1.4 or more can be selected as the functional substance. It is not necessary to set the upper limit of the coefficient, but if illustrated, it may be 20 or less, 15 or less, 10 or less, or 5 or less.

Examples of the functional substance include, but are not limited to, polyphenols. Examples of the polyphenols include lignans, catechins, flavonols, anthocyanins, isoflavones, ferulic acid, ellagic acid, or derivatives thereof. Examples of the lignans can include sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, 2-(3,4-methylenedioxyphenyl)-6-(3-methoxy-4-hydroxyphenoxy)-3,7-dioxabicyclo[3.3.0]octane, 2-(3-methoxy-4-hydroxyphenyl)-6-(3,4-dihydroxyphenyl)-3,7-dioxabicyclo[3.3.0]octane, 2,6-bis(3,4-dihydroxyphenyl)-3,7-dioxabicyclo[3.3.0]octane, and 2-(3,4-methylenedioxyphenyl)-6-(3,4-dihydroxyphenyl)-3,7-dioxabicyclo[3.3.0]octane, and sesamin can be preferably used. Examples of the catechins include epicatechin, epicatechin gallate, epigallocatechin, and epigallocatechin gallate.

The content of the functional substance in the capsule is not particularly limited and can be, for example, 0.15 to 50% by weight, preferably 1.0 to 40% by weight, and more preferably 2.0 to 35% by weight based on the total amount of the capsule.

Gelatin

In the present invention, "gelatin" is used as the wall agent of the capsule. The source of the gelatin is derived is not particularly limited, but examples thereof include pigs (for example, pig skin and pig bones), fish (for example, fish scales and fish skin), and cows (for example, cow bones and cow skin). Gelatin derived from pigs, particularly pig skin, is preferred. The method for producing gelatin is also not particularly limited, and acid-treated gelatin, chemically modified gelatin, gelatin subjected to amphoteric treatment, alkali-treated gelatin, and the like may be used. For example, gelatin can be produced by extracting collagen from a pig, a fish, a cow, or the like by heating, and pretreating the collagen with an acid or an alkali followed by solubilization by hydrolysis. In the present invention, either of alkali-treated gelatin and acid-treated gelatin may be used, but acid-treated gelatin is particularly preferred. Gelatin includes A type and B type, and the isoionic point of the A type is pH 8 to 9, and the isoionic point of the B type is pH 5. In pH between neutral and weakly acidic region, A type gelatin is positively charged, and B type gelatin is negatively charged. Therefore, in the present invention, A type gelatin is preferred, and acid-treated A type gelatin is more preferred. In the present invention, generally available gelatin may be used, and gelatin (product of NACALAI TESQUE, INC.), gelatin (product of Wako Pure Chemical Industries, Ltd.), gelatin (product of Sanko Junyaku Co., Ltd.), gelatin (Nippi, Incorporated), gelatin (Nitta Gelatin Inc.), and the like may be used.

The gelatin that can be used for the capsule can also be selected based on jelly strength. Here, the jelly strength of the gelatin is not particularly limited and can be, for example, 100 g or more, preferably 110 to 180 g, and more preferably 135 to 165 g. Here, the jelly strength can be defined as the load necessary to press down the surface of a jelly, which is prepared by cooling a 6.67% gelatin solution at 10° C. for 17 hours, by 4 mm by a plunger having a diameter of half an inch (12.7 mm) as determined in the quality standard "Animal glues and gelatins", JIS K6503-1996. The jelly strength is measured herein based on the method.

The content of the gelatin is not particularly limited as long as the capsule is formed. The content of the gelatin is, for example, 1 to 30% by weight, preferably 3 to 25% by weight, and more preferably 10 to 20% by weight based on the total amount of the capsule. The content ratio of the functional substance to the gelatin [weight of functional substance:weight of gelatin] is 1:0.01 to 1:1000, preferably 1:0.1 to 1:500, and more preferably 1:1 to 1:200.

Carbodiimide Crosslinking Agent

In the present invention, the "carbodiimide crosslinking agent" refers to a compound that comprises a functional group represented by —N=C=N—, serves as a condensing agent, and can crosslink gelatin. In the present invention, a water-soluble carbodiimide crosslinking agent or a salt thereof is preferably used. The salt includes hydrochlorides and sulfonates. For example, the carbodiimide crosslinking agent or a salt thereof in the present invention includes a water-soluble carbodiimide (1-ethyl-3-(3-dimethylaminopropyl)carbodiimide: WSC) or a salt thereof, 1-cyclohexyl-3-(2-morpholinyl-4-ethyl)carbodiimide (CME-carbodiimide) or a salt thereof, dicyclohexylcarbodiimide (DCC) or a salt thereof, and diisopropylcarbodiimide (DIC) or a salt thereof. The salt compound includes 1-ethyl-3-(3-dimethylaminopropyl)carbodiimide hydrochloride and 1-cyclohexyl-3-(2-morpholinyl-4-ethyl)carbodiimide metho-p-toluenesulfonate. 1-Ethyl-3-(3-dimethylaminopropyl)carbodiimide hydrochloride is particularly preferably used.

The content of the carbodiimide crosslinking agent is not particularly limited, and the concentration before the crosslinking reaction can be 5 to 200 mM, preferably 10 to 150 mM, and more preferably 20 to 100 mM. Alternatively, the content of the carbodiimide crosslinking agent can be defined in relation to the gelatin before the crosslinking reaction. The weight ratio of the gelatin to the carbodiimide crosslinking agent [weight of gelatin:weight of carbodiimide crosslinking agent] before the crosslinking reaction can be, for example, 1:0.06 to 1:0.2, preferably 1:0.08 to 1:0.187, and more preferably 1:0.09 to 1:0.1.

Other Components

The capsule of the present invention may comprise a further functional substance. Examples of the functional substance include vitamins and polyphenols. The content of the further functional substance can be appropriately set. In addition to this, excipients generally used in the fields of foods and drinks, drugs, and cosmetics can also be comprised in the capsule, but this is not limiting. For example, a surfactant, an oil, an alcohol, a humectant, a thickening agent, a preservative, an antioxidant, a chelating agent, a pH adjusting agent, a perfume, coloring matter, an ultraviolet absorbing-scattering agent, a vitamin, an amino acid, and water can be blended.

Characteristics of Capsule

The characteristics of the capsule of the present invention may be evaluated by any method known to those skilled in the art. For example, the shape of the capsule can be evaluated by storing the capsule and then observing the shape of the capsule. The storage may be at room temperature but is preferably performed under conditions in which the temperature, the humidity, and the like are controlled. For example, it is possible to store the capsule under accelerated conditions (for example, 40° C. and 75% RH) or severe conditions (for example, 50° C.±2° C. and 75% RH±5% RH), and observe the shape of the capsule after a lapse of a predetermined period.

The feeling of use of the capsule can also be evaluated after the capsule is stored under conditions similar to the above. The feeling of use of the capsule can be evaluated, for example, based on a feel obtained by applying the capsule to the skin of the fingers, the back of the hand, the inside part of the forearm, or the like for application, or based on a sensation when the capsule is eaten.

It is also possible to analyze other physical properties, for example, texture, hardness, brittleness, adhesiveness, condensability, gum properties, masticability, and elasticity, of the capsule and evaluate whether the capsule has properties suitable for the purpose of use. Such analysis can be performed, for example, by using a texture analyzer (manufactured by SHIMADZU CORPORATION, EZ-X).

<Composition>

The capsules of the present invention may be blended to provide a composition. Examples of the composition include foods and drinks, drugs, or cosmetics comprising the capsules of the present invention. The content of the capsules of the present invention in the composition is not particularly limited and can be, for example, 0.1 to 50% by weight, preferably 0.5 to 30% by weight, and more preferably 1 to 25% by weight based on the total amount of the composition.

The composition of the present invention may comprise one or more surfactants. The surfactant can be one generally used in the fields of foods and drinks, drugs, and cosmetics. Examples of the surfactant include nonionic surfactants, particularly glycerin-based surfactants and sorbitan-based surfactants. Examples of the glycerin-based surfactants include polyglyceryl monooleate. Examples of the sorbitan-based surfactants include polyoxyethylene sorbitan monooleate (20 E.O.).

The composition of the present invention may comprise a further functional substance. Examples of the functional substance include vitamins and polyphenols. The content of the further functional substance can be appropriately set. In addition to this, the composition of the present invention can comprise excipients generally used in the fields of foods and drinks, drugs, and cosmetics, but this is not limiting. For example, a surfactant, an oil, an alcohol, a humectant, a thickening agent, a preservative, an antioxidant, a chelating agent, a pH adjusting agent, a perfume, coloring matter, an ultraviolet absorbing-scattering agent, a vitamin, an amino acid, and water can be blended.

Modes of Use

The composition of the present invention can be applied to cosmetics, foods and drinks, drugs, and the like though not limited. For example, the composition of the present invention can be used as skin external preparations such as skin-whitening cosmetics and quasi-drugs, and foods and drinks such as foods for specified health uses, foods with function claims, foods with nutrient function claims, and supplements. The composition may have any shape such as the shape of a cream, an ointment, an emulsion, a lotion, a solution, a gel, a pack, or a stick.

<Method for Producing Capsule> The method for producing a capsule according to the present invention is not limited, and a capsule can be prepared by any of a chemical method, a physicochemical method, a mechanical method, or a combination thereof. For example, a capsule can be obtained by mixing gelatin and a functional substance, adding a carbodiimide crosslinking agent to crosslink and solidify the gelatin, grinding the solidified gelatin, and recovering the ground material.

As one mode, gelatin and a functional substance are mixed in purified water and heated to 60° C. to dissolve the gelatin, and then a carbodiimide crosslinking agent is added and mixed to crosslink and solidify the gelatin. The solidified gelatin is cut into small pieces and then ground (for example, 7000 rpm, 2 minutes, and room temperature) by Distromix, and then the ground material is transferred to a 1 mm sieve, and the unground material is removed. Then, the ground material is transferred to a 100 μm sieve, and the fraction that does not pass through the sieve can be recovered as capsules.

The functional substance should be a substance that can be included in the capsule of the present invention, and can be appropriately selected according to the purpose of use. The functional substance can be selected based on the water solubility of a substance, and preferably a substance having low water solubility is selected. Here, the substance having low water solubility refers to a substance poorly soluble in water (the amount of a solvent necessary to dissolve 1 g of a solute is 100 mL or more and less than 1000 mL (Nihon Yakkyokuho Kaisetsusho (Manual of the Japanese Pharmacopoeia)), a substance extremely poorly soluble in water (the amount of a solvent necessary to dissolve 1 g of a solute is 1000 mL or more and less than 10000 mL (Nihon Yakkyokuho Kaisetsusho (Manual of the Japanese Pharmacopoeia)), or a substance hardly soluble in water (the amount of a solvent necessary to dissolve 1 g of a solute is 10000 mL or more (Nihon Yakkyokuho Kaisetsusho (Manual of the Japanese Pharmacopoeia)). The water solubility of the substance that can be selected as the functional substance should be, for example, 10 g/L or less, 5 g/L or less, 2 g/L or less, 1.5 g/L or less, or 1.0 g/L or less. It is not necessary to set the lower limit of the water solubility, but if illustrated, it may be 0.0001 g/L or more, 0.001 g/L or more, or 0.005 g/L or more. The functional substance can also be selected based on the octanol/water distribution coefficient (Log Pow) of a substance. For example, a substance having an octanol/water distribution coefficient of 1.0 or more, 1.2 or more, or 1.4 or more can be selected as the functional substance. It is not necessary to set the upper limit of the coefficient, but if illustrated, it may be 20 or less, 15 or less, 10 or less, or 5 or less.

Examples of the functional substance include, but are not limited to, polyphenols. The polyphenols include lignans, catechins, flavonols, anthocyanins, isoflavones, ferulic acid, ellagic acid, or derivatives thereof as described above.

The amount of the functional substance added can be set based on the content of the functional substance in the capsule, the final product. For example, the functional substance can be added so that the content of the functional substance in the entire capsule is 0.15 to 50% by weight, preferably 1.0 to 40% by weight, and more preferably 2.0 to 35% by weight.

In the production of the capsule, gelatin is added. The source of the gelatin is derived is not particularly limited, but examples thereof include pigs (for example, pig skin and pig bones), fish (for example, fish scales and fish skin), and cows (for example, cow bones and cow skin), gelatin derived from pigs, particularly pig skin, is preferred, and so on as described above.

The gelatin used for the production of the capsule can also be selected based on jelly strength. Although not limited, for example, gelatin having a jelly strength of 100 g or more, preferably 110 to 180 g, and more preferably 135 to 165 g can be used. Here, the jelly strength can be defined by a method determined in "Animal glues and gelatins", JIS K6503-1996, as described above.

The amount of the gelatin added can be set based on the gelatin content in the capsule, the final product. For example, the gelatin is added so that the content of the gelatin in the entire capsule is, for example, 1 to 30% by weight, preferably 3 to 25% by weight, and more preferably 10 to 20% by weight. Alternatively, the amount of the gelatin added can also be defined in relation to the functional substance. The weight ratio of the functional substance to the gelatin [weight of functional substance:weight of gelatin] is adjusted at 1:0.01 to 1:1000, preferably 1:0.1 to 1:500, and more preferably 1:1 to 1:200.

In the production of the capsule of the present invention, a carbodiimide crosslinking agent is added to crosslink the gelatin. In the production of the capsule of the present invention, a water-soluble carbodiimide crosslinking agent or a salt thereof is preferably used. The salt includes, but is not limited to, hydrochlorides and sulfonates as described above.

The carbodiimide crosslinking agent can be added at 5 to 200 mM, preferably 10 to 150 mM, and more preferably 20 to 100 mM in terms of concentration before the crosslinking reaction with the gelatin though not limited. Alternatively, the amount of the carbodiimide crosslinking agent added can be defined by the relationship with the gelatin before the crosslinking reaction. The carbodiimide crosslinking agent can be added so that the weight ratio of the gelatin to the carbodiimide crosslinking agent [weight of gelatin:weight of carbodiimide crosslinking agent] before the crosslinking reaction is, for example, 1:0.06 to 1:0.2, preferably 1:0.08 to 1:0.187, and more preferably 1:0.09 to 1:0.1.

In the production of the capsule, in addition to the functional substance, a further functional substance can also be added. Examples of the further functional substance include vitamins and polyphenols as described above. In the production of the capsule, in addition to the above components, excipients generally used in the fields of foods and drinks, drugs, and cosmetics can also be added as described above.

<Method for Producing Composition>

A composition can be produced by blending the capsules of the present invention. The capsules of the present invention can be blended in an amount of 0.15 to 50% by weight, preferably 0.5 to 30% by weight, and more preferably 1 to 25% by weight based on the total amount of the composition.

In the production of the composition, a surfactant generally used in the fields of foods and drinks, drugs, and cosmetics can be further blended as described above.

In the production of the composition, a further functional substance such as a vitamin or a polyphenol can be blended, and excipients generally used in the fields of foods and drinks, drugs, and cosmetics can be blended, as described above.

EXAMPLES

The present invention will be specifically described below by Examples, but the present invention is not limited to these Examples.

Example 1

Study of Capsule Wall Materials

Using various raw materials, functional substance-containing capsules were prepared as described below. The prepared capsules of each type were blended into a cosmetic preparation, and the blend was stored in a constant temperature bath at 40° C. and 75% RH and evaluated by two indicators, a change in color and a feeling of use. As the above cosmetic preparation, the cosmetic preparation shown in Production Example 1 below comprising polysorbate 80, sorbitan sesquioleate, and triethanolamine was used. The physical properties of the functional substance used in this study are a water solubility of 0.82 g/L and an octanol/water distribution coefficient (Log Pow) of 1.6-2.3.

<Preparation of Oil or Fat Capsules>

Each of food hydrogenated oils or fats (beef tallows having a melting point of 41° C., a melting point of 43° C., a melting point of 45° C., and a melting point of 59° C.; rapeseed hydrogenated oil having a melting point of 63° C.; and in addition waxes, 8.8 g) was mixed with the functional substance (1 g) and a lipophilic emulsifier (lecithin or P-100, 0.2 g), and the mixture was heated at 43° C., 45° C., or 47° C. and then stirred at 750 rpm for 10 minutes using a stirrer, to prepare a dispersed phase. Emulsifier MS-3S, water, and methyl cellulose as a thickening agent were mixed, heated at 30° C., 32° C., or 34° C., and stirred at 250 rpm for 10 minutes using a stirrer, to prepare a continuous phase. The dispersed phase was added to the continuous phase, and the mixture was stirred at 250 rpm for 10 minutes using a stirrer, to prepare oil or fat capsules.

<Preparation of Polysaccharide Capsules>

(1) Gellan Gum Capsules

A 0.1 M calcium lactate (150 ml) solution comprising the functional substance (2 g) was added to gellan gum (1.25 g/20 ml) melted at 70° C., and the mixture was ground at 6000 rpm for 5 minutes using Distromix. The ground material was transferred to a 100 sieve, and the fraction that did not pass through the sieve was recovered. The fraction was gellan gum capsules in which the functional substance was included.

(2) Curdlan Capsules

A 3% curdlan solution (0.9 g/30 ml) comprising the functional substance (2 g) was prepared at room temperature, solidified at 80° C. to 90° C., and then ground at 6000 rpm for 5 minutes using Distromix. The ground material was transferred to a 100 μm sieve, and the fraction not passing through the sieve was recovered. The fraction was curdlan capsules in which the functional substance was included.

<Preparation of Gelatin Capsules>

As shown in Table 3, two types of gelatins having different jelly strengths were used. The functional substance (3.0 g) was suspended in a 10% aqueous solution of gelatin (3 g/30 ml of water), and the suspension was heated for dissolution. A water-soluble carbodiimide was added to the solution so as to obtain a final concentration of 20 mM, thereby solidifying the solution. The solidified material was cooled overnight, then preliminarily cut, and then ground using an IKA wet grinder (19,800 $min^{-1}$). The obtained ground material was passed through a 100 µm sieve, and the fraction remaining on the sieve was recovered as gelatin capsules in which the functional substance was included.

<Test Results-1>

The results are shown in Table 1. The capsules comprising the low melting point oils or fats (41° C., 43° C., and 45° C.) as wall agents discolored as time elapsed. It is suggested that during the test period, the shape of the capsules was not maintained, and therefore the functional substance leaked out of the capsules, and discoloration occurred. The changes in the color tones of the capsules comprising the high melting point oils or fats (52° C. and 63° C.) as wall agents were more improved than those of the low melting point oil or fat capsules. From this, it became clear that the melting point of the film oil or fat of the capsules contributed to the suppression of the discoloration of the functional substance or a derivative thereof. On the other hand, when the feeling of use of the high melting point oil or fat capsules was evaluated, it also found that a rough feeling remained, and the feel was poor.

From the above results, it became clear that with the capsules prepared using the oils or fats, it was difficult to achieve both color tone stability and the feeling of use.

<Test Results-2>

As shown in Table 2, for the cream in which the capsules prepared using gellan gum were blended, discoloration was confirmed 1 week after the start of the test, but the feeling of use was good. For the cream in which the capsules prepared using curdlan were blended, discoloration was confirmed 2 weeks after the start of the test, but the feeling of use was not good. When the capsules of either type were blended, a cream that achieved both color tone stability and the feeling of use was not obtained.

TABLE 2

Evaluation of Capsules Using Polysaccharides

| Sample No. | Wall agent | Change in color tone | Feeling of use |
| --- | --- | --- | --- |
| 6 | Gellan gum | Slight discoloration occurred, (week 1) | The cream was fresh, fit comfortably well, and was considerably good |
| 7 | Curdlan | Slight discoloration occurred, (week 2) | The cream was fresh, but not fit comfortably well after application |

<Test Results-3>

As shown in Table 3, for the creams in which the capsules prepared using the gelatins were blended, the color tones of the cream preparations were stable even when 1 month elapsed after the start of the test. This is because the discoloration of the functional substance included in the capsules blended in the cream preparations is suppressed. Further, the feeling of use was good even when compared with that for the capsules prepared with other wall materials.

TABLE 1

Evaluation of Capsules Using Oils or Fats

| Sample No. | Melting point of wall material | Change in cosmetic preparation | Feeling of use |
| --- | --- | --- | --- |
| 1 | 41° C. | The capsules decreased in number, the contents leaked out, and discoloration occurred, (week 1) | When the preparation was massaged on the skin, the capsules were easily crushed, and the feeling of use was good. |
| 2 | 43° C. | The capsules decreased in number, the contents leaked out, and discoloration occurred, (week 1) | When the preparation was massaged on the skin, the capsules were easily crushed, and the feeling of use was good. |
| 3 | 45° C. | The capsules remained, but the contents leaked out, and discoloration occurred, (week 1) | When the preparation was massaged on the skin, the capsules were easily crushed, and the feeling of use was good. |
| 4 | 52° C. | The capsules remained, but the contents leaked out, and slight discoloration was observed, (week 1) | Although the preparation was massaged on the skin, the capsules did not easily fit comfortably, and the feeling of use was not good. |
| 5 | 63° C. | The capsules remained, and no discoloration was observed, (month 1) | Although the preparation was massaged on the skin, the capsules did not fit comfortably, and the feeling of use was not good. |

TABLE 3

Evaluation of Capsules Using Gelatins

| Sample No. | Gelatin (jelly strength) | Change in cosmetic preparation | Feeling of use |
|---|---|---|---|
| 8 | APS150F (135 to 165 g) | The capsules remained, and the extent of discoloration was slight, (month 1) | When the cream was massaged on the skin, the capsules were easily crushed, and the feeling of use was considerably good. |
| 9 | T20H (128 to 152 g) | The capsules remained, and the extent of discoloration was slight, (month 1) | When the preparation was massaged on the skin, the capsules were easily crushed, and the feeling of use was good. |

Example 2

Influence of Jelly Strength on Characteristics of Capsules

<Preparation of Samples>

Each of 10% aqueous solutions of gelatins having different jelly strengths as shown in Table 4 (3 g/30 ml of water) was heated for dissolution. A water-soluble carbodiimide was added to the solution so as to obtain a final concentration of 50 mM, thereby solidifying the solution. The solidified material was cooled overnight, preliminarily cut, and then ground using an IKA wet grinder (19,800 min$^{-1}$). The obtained ground material was passed through a 100 μm sieve, and the fraction remaining on the sieve was recovered as crosslinked gelatin capsules (15 g). The jelly strength of each gelatin shown in Table 4 is defined as the load necessary to press down the surface of a jelly, which is prepared by cooling a 6.67% gelatin solution at 10° C. for 17 hours, by 4 mm by a plunger having a diameter of half an inch (12.7 mm) as determined in the quality standard "Animal glues and gelatins", JIS K6503-1996.

<Test Method>

The capsules of each type prepared as described above were blended at 20% by weight into an emulsion preparation. The blend was subjected to an accelerated stability test at 40° C.±2° C. and 75% RH±5% RH and a severe test at 50° C.±2° C. and 75% RH±5% RH, and the shape and feeling of use of the capsules were evaluated. As the above emulsion preparation, the emulsion shown in Production Example 2 below was used.

<Test Results>

The results are shown in Table 4. For the tested capsules of all types, the shape of the capsules was maintained. Any capsules tested were shown to have a good feeling of use, and, in particular, the capsules produced using the gelatin having a jelly strength of 135 to 165 g showed the best result. From these results, it was suggested that the capsules achieved both shape stability and the feeling of use.

TABLE 4

Influence of Jelly Strength on Shape and Feeling of Use of Capsules

| Gelatin (jelly strength) | 40° C. | 50° C. | Feeling of use |
|---|---|---|---|
| APS150F (135 to 165 g) | The shape was stable at the point in time when 2 months | | ⊚ |
| BCN200S (185 to 215 g) | elapsed | | ○ |
| BCN330SL (320 to 350 g) | | | ○ |

Example 3

Evaluation of Texture of Capsules

<Preparation of Samples>

Aqueous solutions in which various gelatins were suspended (Table 5) were stirred at 65° C. for 5 minutes to dissolve the gelatins. A water-soluble carbodiimide (WSC) was added to the solutions at the final concentration (50 mM or 100 mM) shown in Table 5 to solidify the solutions. The solidified materials without being ground were subjected to the following test as capsules (samples 4 to 12).

TABLE 5

Compositions of Capsules

| Sample | Gelatin | WSC |
|---|---|---|
| 4 | 10% By weight APS150F | 50 mM |
| 5 | 10% By weight BCN200S | 50 mM |
| 6 | 10% By weight BCN330SL | 50 mM |
| 7 | 10% By weight APS150F | 100 mM |
| 8 | 10% By weight BCN200S | 100 mM |
| 9 | 10% By weight BCN330SL | 100 mM |
| 10 | 10% By weight APS150F | 50 mM |
| 11 | 20% By weight BCN200S | 50 mM |
| 12 | 20% By weight BCN330SL | 50 mM |

<Test Method>

The texture, hardness, brittleness, adhesiveness, condensability, gum properties, masticability, and elasticity of samples 4 to 12 prepared above were analyzed using a texture analyzer (Shimadzu Techno-Research, Inc.). For the analysis of texture, a two-bite method performed by applying pressure to a gel two times, which was used as a method for analyzing foods for elderly people, was used. The analysis conditions were shown below.

Type of machine: EZ-X (manufactured by Shimadzu Techno-Research, Inc.)
Speed: 1 mm/sec
Test jig: universal design food
Entry distance: 13.3 mm
Temperature: room temperature (23° C.)
Load cell capacity: 500 N
Type of test: compression (two compressions)
elongation origin: test force 1 gf
Plunger: diameter ((p) 20 mm <Analysis Results>

The results of the texture analysis are shown in FIG. 1. The gel strength of samples 7 to 9 was low, and the gel strength decreased more by the second compression than by the first compression. From these results, it is suggested that for the capsules solidified with 100 mM WSC, the shape is stably maintained during storage, but the gel strength decreases each time force is applied to the capsules during use, and finally the capsules are broken. Such characteristics make it possible to rapidly spread the capsules over the entire skin surface without causing a rough feeling. Such characteristics also make it possible to eat the capsules without causing a rough mouthfeel and gradually break the capsules by mastication, digestion in the body, and the like. The capsules of the present invention are excellent in the feeling of use and can be applied to foods and drinks and skin external preparations such as cosmetics and quasi-drugs.

The results of analyzing the hardness, brittleness, adhesiveness, condensability, gum properties, masticability, and elasticity of samples 4 to 12 are shown in Table 6. It became clear that the numerical values of masticability, brittleness, aggregability, gum properties, and elasticity of samples 7 to 9 were significantly lower than those of other samples. The low numerical values of masticability and brittleness mean that samples 7 to 9 are brittle and collapse easily. The low numerical values of gum properties and elasticity mean that samples 7 to 9 have adhesiveness. In other words, it is suggested that when samples 7 to 9 are used to form cosmetics or skin external preparations, the capsules can be easily collapsed by applying friction to the capsules on the skin, and therefore the capsules hardly cause roughness, and the capsules easily stick to the skin and therefore easily fit comfortably on the skin. It is suggested that when samples 7 to 9 are used to form foods or drinks, it is possible to eat the capsules without causing a rough mouthfeel and gradually break the capsules by mastication, digestion in the body, and the like. Therefore, it is suggested that when a functional substance is not included, preferably the capsules solidified with 100 mM WSC are excellent in the feeling of use when applied to the skin as skin external preparations or when eaten or drunk as foods or drinks. It is also considered that when a functional substance is included in capsules, the elasticity of the capsules increases or decreases compared with the case where a functional substance is not included. Therefore, when a functional substance is included in capsules, it is also possible to adjust the concentration of WSC at 100 mM or less as needed and solidify the capsules in order to achieve efficient release of the functional substance in addition to the above excellent feeling of use.

As described above, it can be understood that the conclusion derived from the analysis of texture by the two-bite method (FIG. 1) matches the conclusion derived from the analysis of hardness, brittleness, adhesiveness, condensability, gum properties, masticability, and elasticity (Table 6). Therefore, it is suggested that the texture by the two-bite method can be applied as a simpler indicator of capsule making (particularly the texture of capsules).

TABLE 6

Physical Properties of Capsules

| Sample | Hardness_test force calculated for entire area (gf) | Brittleness (gf) | Adhesiveness (second intersection point to next intersection point) (kgf · mm) | Condensability | Gum properties | Masticability | Elasticity |
|---|---|---|---|---|---|---|---|
| 4 | 3987.64 | 329.645 | −0.2943 | 0.77706 | 3098.65 | 2966.25 | 0.95727 |
| 5 | 3124.80 | 264.287 | −0.0182 | 0.76248 | 2382.60 | 2533.50 | 1.06334 |
| 6 | 5569.00 | 251.142 | −0.1203 | 0.83721 | 4662.43 | 6895.72 | 1.47900 |
| 7 | 3069.61 | 78.9408 | −0.0004 | 0.54834 | 1683.20 | 862.534 | 0.51244 |
| 8 | 2098.61 | 99.7763 | −0.1861 | 0.55959 | 1174.36 | 756.480 | 0.64416 |
| 9 | 3452.11 | 408.222 | −0.2454 | 0.47968 | 1655.92 | 975.190 | 0.58891 |
| 10 | 4889.11 | — | −0.0168 | 1.03485 | 5059.49 | 5177.96 | 1.02342 |
| 11 | 6848.95 | — | −0.0166 | 0.95051 | 6510.00 | 6899.92 | 1.05990 |
| 12 | 8482.42 | — | −0.0087 | 0.94050 | 7977.69 | 8640.18 | 1.08304 |

Example 4

Preparation of Finely Ground Capsules Comprising Functional Substances

<Preparation of Capsules Comprising Sesamin>

H20T (derived from pig skin, product of Nippi, Incorporated) (3 g/30 mL of water) and sesamin (water solubility 0.0066 g/L, octanol/water distribution coefficient (Log Pow) 4.1) (6.0 g) were mixed, and stirred at 65° C. for 5 minutes to dissolve the gelatin. 0.28 g of a water-soluble carbodiimide (product of NACALAI TESQUE, INC., final concentration 50 mM) was added to the solution to crosslink and solidify the gelatin. 100 mL of purified water was added, and the mixture was stirred at 6000 rpm for 5 minutes using Distromix, to grind the solids. The ground material was transferred to a 100 μm sieve, and the fraction remaining on the sieve was recovered as capsules comprising sesamin.

In order to confirm that sesamin was contained in the capsules prepared as described above, 1 g of the capsules were weighed into a centrifugal tube and suspended in 10 mL of dimethyl sulfoxide (DMSO). The suspension was heated at 80° C. for 10 minutes, and then the centrifugal tube was stirred by a vortex mixer. The stirred liquid was subjected to centrifugation (3500 rpm, 10 min, 25° C.). The supernatant was recovered and used as an HPLC sample. Sesamin was detected and quantified under the following conditions. As a result, it became clear that 10 mg of sesamin was present per g of the capsules. Thus, it was confirmed that sesamin was included in the capsules.

| HPLC Analysis Conditions of Sesamin | |
|---|---|
| Column | Develosil C30 UG-5 (4.6 mm × 150 mm: manufactured by Nomura Chemical Co., Ltd.) |
| Mobile phase | Buffer A: distilled water comprising 0.1% formic acid |
| | Buffer B: 80% acetonitrile (AcCN)/distilled water comprising 0.1% formic acid |

| HPLC Analysis Conditions of Sesamin | |
|---|---|
| Detection wavelength | 280 nm |
| Flow rate | 1 ml/min |
| Amount of sample | 10 μL/injection |
| Program | 20% Buffer B → 100% Buffer B (linear gradient: 40 minutes) |

<Preparation of Capsules Comprising Ferulic Acid>

H20T (derived from pig skin, product of Nippi, Incorporated) (3 g/30 mL of water) and ferulic acid (water solubility 0.91 g/L, octanol/water distribution coefficient (Log Pow) 1.6-1.7) (6.0 g) were mixed, and stirred at 65° C. for 5 minutes to dissolve the gelatin. 0.56 g of a water-soluble carbodiimide (product of NACALAI TESQUE, INC., final concentration 100 mM) was added to the solution to crosslink and solidify the gelatin. 100 mL of purified water was added, and the mixture was stirred at 6000 rpm for 5 minutes using Distromix, to grind the solids. The ground material was transferred to a 100 μm sieve, and the fraction remaining on the sieve was recovered as capsules comprising ferulic acid (capsules 2).

In order to confirm that ferulic acid was contained in the capsules prepared as described above, 1 g of the capsules were weighed into a centrifugal tube, and an HPLC analysis sample was prepared according to the method shown above. Ferulic acid was detected and quantified under the following conditions. As a result, it became clear that 6.95 mg of ferulic acid was present per g of the capsules. Thus, it was confirmed that ferulic acid was included in the capsules.

| HPLC Analysis Conditions of Ferulic Acid | |
|---|---|
| Column | Develosil C30 UG-5 (4.6 mm × 150 mm: manufactured by Nomura Chemical Co., Ltd.) |
| Mobile phase | Buffer A: distilled water comprising 0.1% formic acid |
| | Buffer B: 80% acetonitrile (AcCN)/distilled water comprising 0.1% formic acid |
| Detection wavelength | 254 nm |
| Flow rate | 1 ml/min |
| Amount of sample | 10 μL/injection |
| Program | 5% Buffer B → 60% Buffer B (linear gradient: 40 minutes) |

Production Example 1

Cream

A cream was produced by the formulation shown in Table 7. Section A that was an oil-soluble component and section B that was a water-soluble component were each heated and dissolved at 75° C. Then, while section A was stirred in a homomixer at 5000 rpm, section B was added for emulsification to form an O/W emulsion. Then, the O/W emulsion was cooled to 60° C., and section C was added. The mixture was further cooled to 40° C., and section D was added to produce the objected cream.

TABLE 7

| Section | Component name | Amount blended (%) |
|---|---|---|
| A | Cetanol | 3 |
| | Glyceryl stearate | 1.2 |

TABLE 7-continued

| Section | Component name | Amount blended (%) |
|---|---|---|
| | Stearic acid | 2 |
| | Batyl alcohol | 1 |
| | Microcrystalline wax | 1 |
| | Di(phytosteryl/octyldodecyl) lauroylglutamate | 3 |
| | Polysorbate 80 | 0.5 |
| | Sorbitan sesquioleate | 0.3 |
| B | Water | to make a total of 100 |
| | Glycerin | 5 |
| | BG | 10 |
| | Phenoxyethanol | 0.3 |
| | Triethanolamine | 0.5 |
| C | 1% liquid of carboxyvinyl polymer | 15 |
| D | Functional substance-comprising gelatin capsules | 20 |

Production Example 2

Emulsion

An emulsion was produced by the formulation shown in Table 8. Section A that was a water-soluble component and section B that was an oil-soluble component were each heated and dissolved at 75° C. Then, while section A was stirred in a homomixer at 5000 rpm, section B was added for emulsification to form an O/W emulsion. Then, the O/W emulsion was cooled to 60° C., and section C was added. The mixture was further cooled to 40° C., and section D was added to produce the objective emulsion.

TABLE 8

| Section | Component name | Amount blended (%) |
|---|---|---|
| A | Cetanol | 0.3 |
| | Behenyl alcohol | 0.3 |
| | Glyceryl stearate | 0.6 |
| | Batyl alcohol | 0.5 |
| | Polyglyceryl monostearate | 0.3 |
| | Di(phytosteryl/octyldodecyl) lauroylglutamate | 2 |
| | Triethylhexanoin | 5 |
| | Liquid paraffin | 5 |
| | Polysorbate 80 | 0.5 |
| | Sorbitan sesquioleate | 0.3 |
| B | Water | to make a total of 100 |
| | Glycerin | 5 |
| | BG | 10 |
| | Phenoxyethanol | 0.3 |
| | Na hydroxide | 0.065 |
| C | 1% liquid of carboxyvinyl polymer | 15 |
| D | Functional substance-comprising gelatin capsules | 20 |

Effects Achieved by Modes of Present Invention Shown in Present Examples

In the present invention, it has been found that a capsule having a stable shape can be produced by crosslinking gelatin that is a wall substance using a carbodiimide crosslinking agent. The capsule does not produce a feeling of roughness when applied to the skin or eaten, even if stored for a long period, and has an excellent feeling of use. Further, the capsule can be easily collapsed during use and therefore can suitably release the functional substance. Such specification is advantageous when the capsule is used for foods and drinks and external preparations for skin such as cosmetics and quasi-drugs.

The invention claimed is:

1. A method for producing a capsule, comprising steps of: mixing gelatin and a functional substance, wherein the gelatin has a jelly strength of 110 g to 180 g, and wherein the functional substance has a water solubility of 10 g/L or less, and is selected from the group consisting of: a lignan, a catechin, a flavonol, an anthocyanin, an isoflavone, ferulic acid, and ellagic acid; crosslinking the gelatin by only reacting with a carbodiimide crosslinking agent; solidifying the crosslinked gelatin; and grinding the solidified gelatin to obtain the capsule.

2. The production method according to claim 1, wherein the gelatin is crosslinked in a solution comprising the carbodiimide crosslinking agent at a concentration of 5 mM to 200 mM.

3. The production method according to claim 1, wherein the gelatin and the carbodiimide crosslinking agent are reacted at a concentration ratio of 1:0.06 to 1:0.2.

4. The production method according to claim 1, wherein the carbodiimide crosslinking agent is selected from the group consisting of 1-ethyl-3-(3-dimethylaminopropyl)carbodiimide, 1-cyclohexyl-3-(2-morpholinyl-4-ethyl)carbodiimide, dicyclohexylcarbodiimide, diisopropylcarbodiimide, and salts thereof.

5. A capsule comprising (i) a functional substance and (ii) gelatin crosslinked only by reacting with a carbodiimide crosslinking agent, wherein the functional substance has a water solubility of 10 g/L or less, and is selected from the group consisting of: a lignan, a catechin, a flavonol, an anthocyanin, an isoflavone, ferulic acid, and ellagic acid, and wherein the gelatin has a jelly strength of 110 g to 180 g.

6. The capsule according to claim 5, wherein the gelatin has a jelly strength of 135 g to 165 g.

7. The capsule according to claim 5, wherein the gelatin is acid-treated gelatin.

8. The capsule according to claim 5, wherein the functional substance is sesamin or ferulic acid.

* * * * *